(12) United States Patent
Chmielewski

(10) Patent No.: US 8,759,509 B2
(45) Date of Patent: Jun. 24, 2014

(54) WAY OF USING THERMOLABILE GROUPS TO PROTECT HYDROXYL FUNCTIONS AND COMPOUNDS FOR IMPLEMENTING THE PROCEDURE

(75) Inventor: Marcin Krzysztof Chmielewski, Poznan (PL)

(73) Assignee: Instytut Chemii Bioorganicznej Polskiej Akademii Nauk, Poznan (PL)

( * ) Notice: Subject to any disclaimer, the term of this patent is extended or adjusted under 35 U.S.C. 154(b) by 0 days.

(21) Appl. No.: 13/702,241

(22) PCT Filed: Jun. 1, 2011

(86) PCT No.: PCT/PL2011/000055
§ 371 (c)(1),
(2), (4) Date: Dec. 5, 2012

(87) PCT Pub. No.: WO2011/155855
PCT Pub. Date: Dec. 15, 2011

(65) Prior Publication Data
US 2013/0085272 A1 Apr. 4, 2013

(30) Foreign Application Priority Data
Jun. 10, 2010 (PL) .......................... 391468

(51) Int. Cl.
*C07H 21/00* (2006.01)
(52) U.S. Cl.
USPC ...................... 536/25.31; 536/25.3
(58) Field of Classification Search
None
See application file for complete search history.

(56) References Cited

U.S. PATENT DOCUMENTS 7,612,197 B2    11/2009  Beaucage et al.

OTHER PUBLICATIONS

Chmielewski Organic Letters (2009), vol. 11, pp. 3742-3745.*
Chmielewski, Marcin K. et al., "Thermolytic Carbonates for Potential 5'-Hydroxyl Protection of Deoxyribonucleosides," J. Org. Chem., 2003, vol. 68, pp. 10003-10012.
International Search Report issued in International Patent Application No. PCT/PL2011/000055 mailed Nov. 24, 2011.
Chmielewski; "Protecting of a Thermolabile Protecting Group: 'Click-Clack' Approach", Organic Letters, 2009, vol. 11, No. 16, American Chemical Society, pp. 3742-3745, Jul. 27, 2009.

* cited by examiner

*Primary Examiner* — Patrick Lewis
(74) *Attorney, Agent, or Firm* — Oliff PLC

(57) ABSTRACT

A procedure for using thermolabile groups to protect a hydroxyl function, above all in nucleosides, nucleotides, oligomers, nucleic acids during the reactions of organic synthesis. Various new compounds that can be used to implement the procedure. The way of using thermolabile groups to protect hydroxyl functions consists in a primary, secondary and tertiary hydroxyl group converting into a groups during the reaction between a compound and a compound whose hydroxyl group is to be blocked. The blocking reaction is carried out by means of widely known methods appropriate for that purpose in the presence of a chemically basic catalyst. The obtained product has its hydroxyl group blocked. Then the compound with the group blocked can be used for the purposes of various chemical processes. After their completion, the hydroxyl group is unblocked by dissolving it in a solvent at a temperature of 50-95° C.

14 Claims, 19 Drawing Sheets

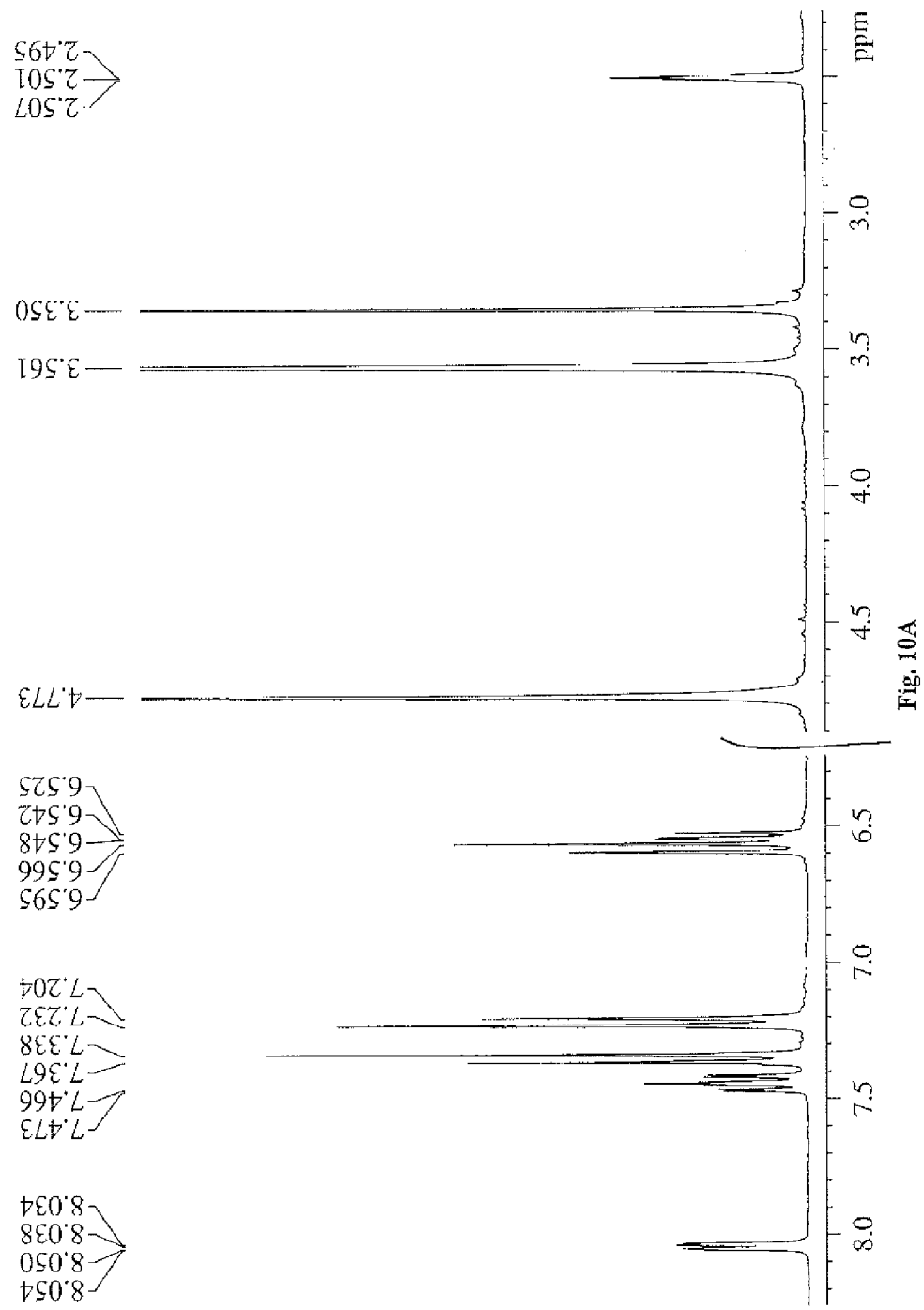

WAY OF USING THERMOLABILE GROUPS TO PROTECT HYDROXYL FUNCTIONS AND COMPOUNDS FOR IMPLEMENTING THE PROCEDURE

The subject of the invention is a new way of using thermolabile groups to protect a hydroxyl function, above all in nucleosides, nucleotides, oligomers and nucleic acids during the reactions of organic synthesis. The invention also covers new compounds that can be used, for example, to implement the procedure.

The protective groups presented in specialist literature are used in organic syntheses when it is necessary to carry out a selective chemical reaction in a given place without disturbing other reactive parts of a molecule of amine groups, carboxylic acids, hydroxyl groups, phosphates, and the like. Being protected by such groups, reactive places of the molecule do not participate in the chemical reaction, where the unprotected parts of the same molecule undergo transformation. The use of protective groups is very often the only way to carry out a synthesis of chemical compounds of a particular class. Their usefulness and functionalities are determined on the basis of their features, including: the manner of blocking a reactive part of a molecule; durability during a chemical process; removal of the group after a stage of a synthesis has been completed. In practice, protective groups are most often used to secure hydroxyl, amine and phosphate functions.

The protective groups of hydroxyl functions are most frequently used, and are of crucial importance to organic syntheses. Such groups are especially useful in the synthesis of oligonucleotides, which are a subject of extensive research and development activities, not least because they have great potential of therapeutic applications.

Chemical literature, "Chmielewski M. K., Marchan V., Cieslak J., Grajkowski A., Livengood V., Munch U., Wilk A., Beaucage S. L., J. Org. Chem. 2003, 68, 10003-10012", presents 2-[N-pyridyl-N-methyl]-1-phenylcarboxyethylamine as the most effective protective group of a hydroxyl function with the asymmetric centre in the achiral carbon α.

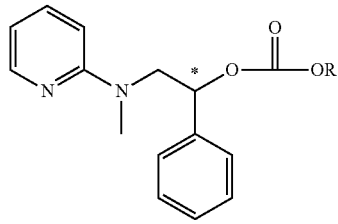

The presence of the phenyl group beside the carbon atom considerably precipitates the unblocking reaction, while creating an asymmetric centre in that place and giving rise to the formation of a racemic mixture. A mixture of diastereomers is obtained as a result of using this group to protect a hydroxyl group (or similar one) in a chiral molecule of a specific configuration. The existence of the centre of symmetry in a protective group is a flaw, hampering as it does further manipulation of a blocked molecule on account of using not a pure compound, but a mixture.

Instability at lower temperatures is another drawback of known thermolabile protecting groups. The reason lies in the fact that the manipulation of a molecule containing thermolabile protecting groups is limited, since a protecting group is unintentionally unblocked when it is required that the reactive place of the molecule be completely protected. The instability level reaches 10% within 24 hours.

The method is well-known that the durability of a thermolabile protecting group can be raised by using a nitro group placed in a pyridyl ring, as described in the U.S. Pat. No. 7,612,197 (this group deactivates the pyridyl ring and stops the therodeprotection reaction). In consequence of the reduction, the nitro group converts into an amine group. Providing electrons to the pyridyl ring, the amine group makes it highly unstable and susceptible to thermal unblocking. This approach is complicated and requires the use of titanium chloride III ($TiCl_3$).

From the same patent description comes the manner of protecting alcohol's hydroxyl group of the formula Pg-O—R, where Pg is a protective group of the following formula:

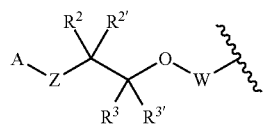

where:
A is a 2-pirydyl;
Z is CH2 or NR1,
R1, R2, R2', R3 and R3' are the same or different, and each can be for example: H, alkil or alkil containing an aryl substituent;
W is CO, CS or SO
R stands for organic hydroxyl residues of the alcohol protected.

The aim of thermolabile protecting groups is to block a hydroxyl function so as to prevent it from undergoing undesired reactions. Then the blocking group is removed as a result of the effect of higher temperature, and the hydroxyl unit is reconstructed.

Long unblocking time is a flaw of known thermolabile protecting groups. The most labile groups are characterised by an total unblocking time ranging from 10 to 20 minutes, poor durability at room temperatures, and the formation of the mixture of diastereomers during the blocking of the reactive part of the molecule. The invention is aimed at improving the protection of a hydroxyl function, especially in nucleosides, nucleotides oligomers and nucleic acids during the reactions of organic synthesis in particular.

New compounds of general formula 1, where $R^1$ stands for H or $CH_3$, O, NH, $C_6H_5$, $CH_2C_6H_5$; $R^2$ stands for H; $R^3$, $R^4$, $R^5$, $R^6$, $R^7$ are equal or different, and stand for H or $NH_2$, OH, $OCH_3$, $NO_2$, $C(O)OCH_3$, $C(O)OC_2H_5$, a halogen; where $R^8$ stands for $CH_3$, OH or $CH_2OH$, O, an alkene (with the main chain containing 1-5 carbon atom(s) and one double bond), $CH(CH_3)C_6H_5$, $CH_3NR^9$, where $R^9$ stands for H or $CH_3$, O, NH, $C_6H_5$, $CH_2C_6H_5$.

BRIEF DESCRIPTION OF THE DRAWINGS

FIGS. 10A and 10B are illustrations of the $^1$HNMR and $^{13}$CNMR spectra of the compound obtained from Example 16;

Figure 1:
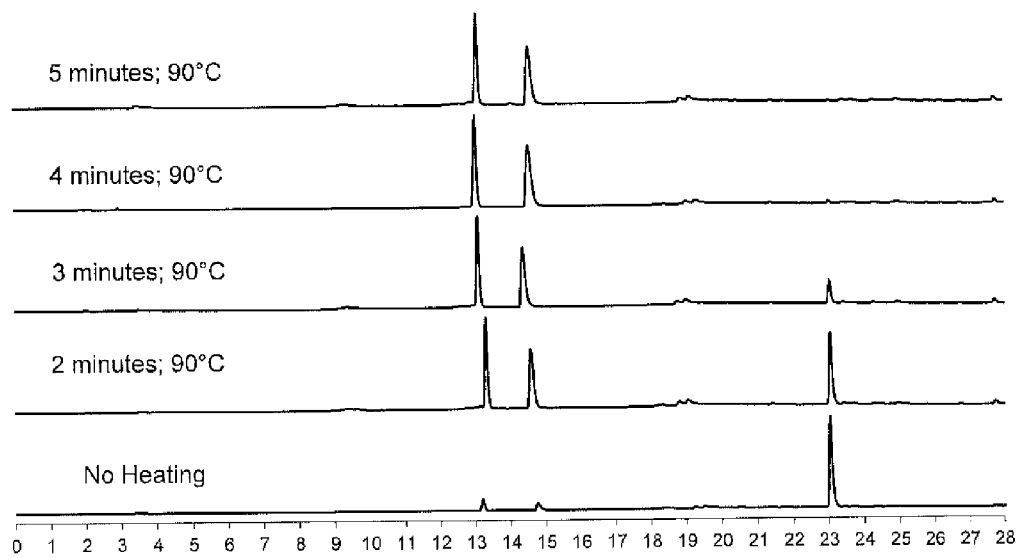
FIG. 1 is an illustration of the kinetic decomposition (based on a HPLC analysis) of the compound depicted in FIG. 3.

New compounds of general formula 3, where $R^1$ stands for H or $CH_3$, O, NH, $C_6H_5$, $CH_2C_6H_5$; where $R^2$ stands for H; $R^3$, $R^4$, $R^5$, $R^6$, $R^7$ are equal or different and stand for H or $NH_2$, OH, $OCH_3$, $NO_2$, $C(O)OCH_3$, $C(O)OC_2H_5$ a halogen; $R^8$ is $CH_3$, OH or $CH_2OH$, O, an alkene with the main chain containing 1-5 atom carbon(s) and one double bond, $CH(CH_3)C_6H_5$, $CH_3NR^9$, where $R^9$ stands for H or $CH_3$, O, NH, $C_6H_5$, $CH_2C_6H_5$; R stands for the rest of the protected molecule.

The compounds of general formula 2 are transitional products (precursors), used to obtain the compounds of general formula 1.

The compounds of general formula 2, where $R^1$ to $R^8$ stand for the above, are obtained from the reaction between an appropriate pyridine derivative of general formula 4, where $R^8$ stands for the above, and accordingly substituted N-benzylethanolamine of general formula 5 or aminoalcohol of formula 6, and then with benzyl bromide of formula 7, where the substituents $R^1$ to $R^7$ stand for the above. To carry out the reaction, it is necessary to use a reflux condenser for heating at a temperature of 60-160° C. in a solvent of tetrahydrofuran, xylene, or toluene. The time needed for the conversion is 12 to 36 hours, while the time required for the reaction to finish depends on the solvent used and the temperature of reaction. Then a compound of general formula 2 is isolated by means of known methods.

The compounds of general formula 1, where $R^1$ to $R^8$ stand for the above, are obtained by dissolving an appropriate compound of general formula 2, where $R^1$ to $R^8$ stand for the above, in dry acetonitrile. Then such a compound is mixed with a carbonylating agent (beneficially with 1,1'-carbonyldiimidazole). The process is carried out at a room temperature. It takes the compound 30 minutes to convert completely.

The method of using thermolabile groups to protect a hydroxyl function, consisting in securing the primary, secondary and tertiary hydroxyl groups of nucleosides, nucleotides oligomers, and nucleic acids in particular during the reactions of organic synthesis, is characterized by the conversion of the primary, secondary and tertiary hydroxyl group of nucleosides, nucleotides oligomers, and nucleic acids into a group of general formula 3. The conversion is based on the reaction between a compound of general formula 1, where $R^1$ to $R^8$ stand for the above, and a compound whose hydroxyl group is to be blocked. The blocking reaction is carried out by means of known methods, appropriate for that purpose, and in the presence of chemically basic catalyst, (beneficially with 1,1,3,3-tetramethylguanidine).

With the hydroxyl group blocked, the compound can used in various chemical processes. And after the completion thereof, the group can be unblocked.

For that purpose, the compound blocked should be first dissolved, and then heated at 50-95° C., 70-90° C. being most beneficial. In unblocking it is advisable to use an alcohol from the following group: acetonitrile; alcohol forming a homogenous mixture with water; water buffer of a pH of 6-8. A mixture of acetonitrile with a water buffer of a pH of 6-8, the content of the former being 5% to 50% (volume percent), and the concentration of the blocked form in the mixture of acetonitrile with the water buffer of a pH 6-8 being 0.5 mole to 0.01 millimole—it is beneficial if the volume fraction of acetonitrile in the mixture is 10%-30%, and the concentration of the blocked form in the mixture of acetonitrile with the water buffer of a pH of 6-8 is 0.2 mole to 1 millimole. A different mixture of alcohol and a water buffer of a pH of 6-8 can also be used, consisting of 5% to 50% of the former, with the concentration of the blocked form being 0.5 mole to 0.01 millimole; it is beneficial if the volume fraction of alcohol in the mixture with the water buffer of a pH 6-8 is 10% to 30%, with the concentration of the blocked form at a level of 0.2 mole to 1 millimole. In the unblocking process, as a solvent it is advisable to use a water buffer of a pH of 7, or mixture of acetonitrile with a water buffer of a pH of 7, or a mixture of water buffer of a pH of 7.

As regards protection, the invention suggests using the hydroxyl group of new compounds of general 1, where $R^1$ stands for H; $R^2$ stands for H; $R^3$, $R^4$, $R^5$, $R^6$, $R^7$ are equal and stand for H; $R^8$ stands for H.

The invention suggests using the hydroxyl group of new compounds of general formula 1, where $R^1$ stands for H; $R^2$ stands for H; $R^3$, $R^4$, $R^5$, $R^6$, $R^7$ are different and stand for H or a halogen; $R^8$ stands for H; especially beneficial is the use of the compounds where $R^3$ and $R^5$ stand for a halogen (F or Cl or Br), and $R^4$, $R^6$, $R^7$ stand for H; and $R^8$ denotes H.

The invention suggests using the hydroxyl group of new compounds of general formula 1, where $R^1$ stands for H; $R^2$ stands for H; $R^3$, $R^4$, $R^5$, $R^6$, $R^7$ are different and stand for H or $NO_2$; and $R^8$ stands for H; especially beneficial is the use of the compounds where $R^5$ stands for $NO_2$, and $R^3$, $R^4$, $R^6$, $R^7$ denote H.

The invention suggests using the hydroxyl group of new compounds of general formula 1, where $R^1$ stands for H; $R^2$ stands for H; $R^3$, $R^4$, $R^5$, $R^6$, $R^7$ stand for H; and $R^8$ stands for $CH_3$.

The invention suggests using the hydroxyl group of new compounds of general formula 1, where $R^1$ stands for $C_6H_5$; $R^2$ stands for H; $R^3$, $R^4$, $R^5$, $R^6$, $R^7$ are equal and stand for H; and $R^8$ stands for H.

The invention suggests using the hydroxyl group of new compounds of general formula 1, where $R^1$ stands for H; $R^2$ stands for H; $R^3$, $R^4$, $R^5$, $R^6$, $R^7$ are different and stand for H or $C(O)OCH_3$; $R^8$ stands for H; especially beneficial is the use of the compounds where $R^5$ stands for $C(O)OCH_3$.

The compounds of general formula 1 can be used in organic syntheses to protect primary, secondary and tertiary hydroxyl groups of nucleosides, nucleotides oligomers, nucleic acids (especially during the synthesis of ribonucleic acid with a view to securing the position of the second sugar ring), derivatives of nucleic acids, polypeptides, sugars, polysaccharides, and proteins. They can also be used for protecting reactive hydroxyl functional groups during the synthesis of many biomolecules, such as: nucleosides, nucleotides oligomers, nucleic acids, their derivatives, proteins, polypeptides, sugars, polysaccharides and others; as well as for the purposes of the organic synthesis of other chemical compounds which require that hydroxyl groups be protected selectively; and for the needs of organic syntheses and reactions involving enzymes, in which case it is necessary to unblock functional groups selectively in physiological conditions of neutral pH.

The solution as based on the invention is helpful in that it improves the protection of a hydroxyl function with the assistance of new compounds defined in the invention description, and raises the durability of a blocking hydroxyl group at room temperatures, as well as considerably shortens the time needed for unblocking a protected hydroxyl group.

Figure 5A:
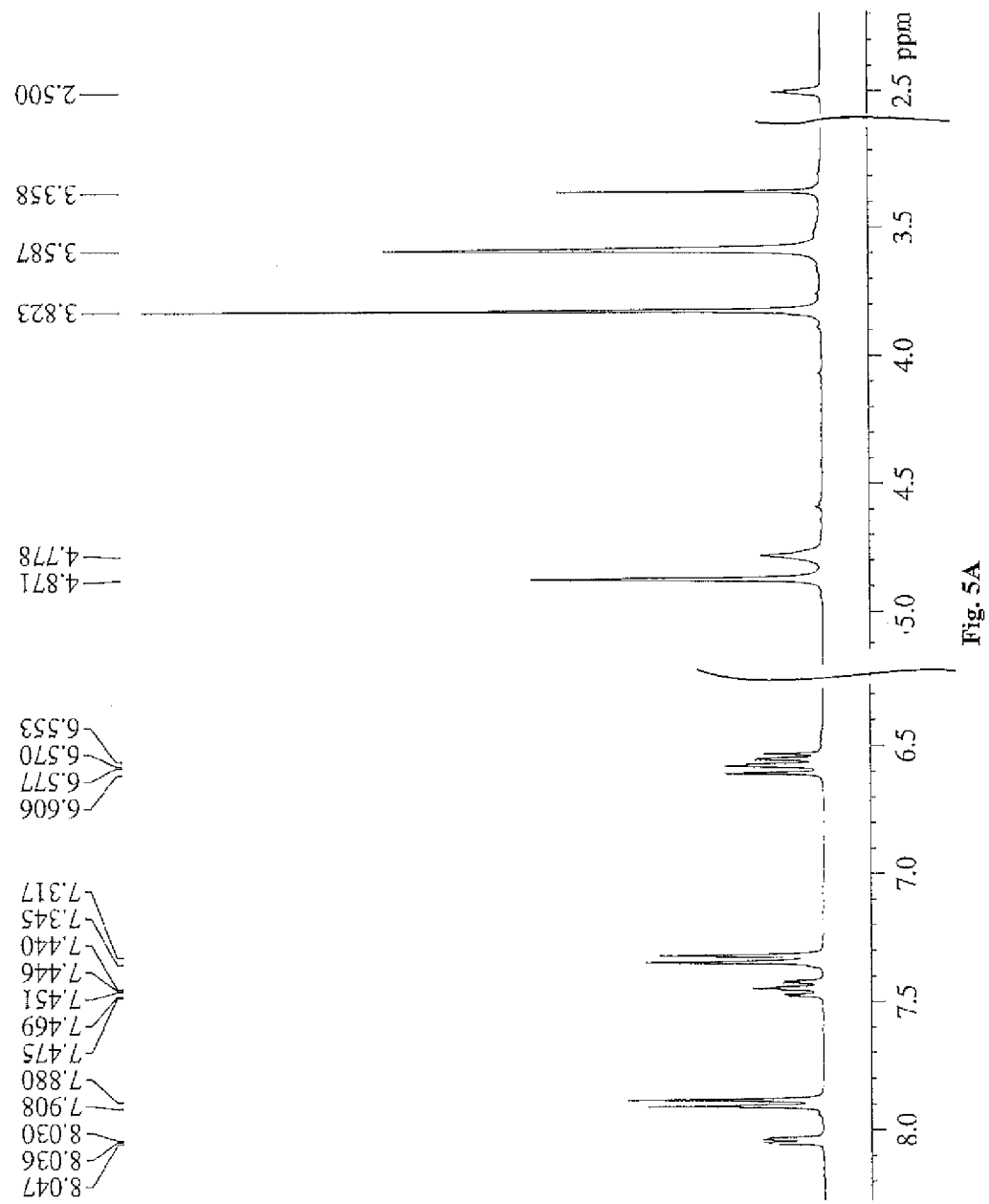
FIGS. 5A and 5B are illustrations of the $^1$HNMR and $^{13}$CNMR spectra of the compound obtained from Example 1.
Figure 5B:
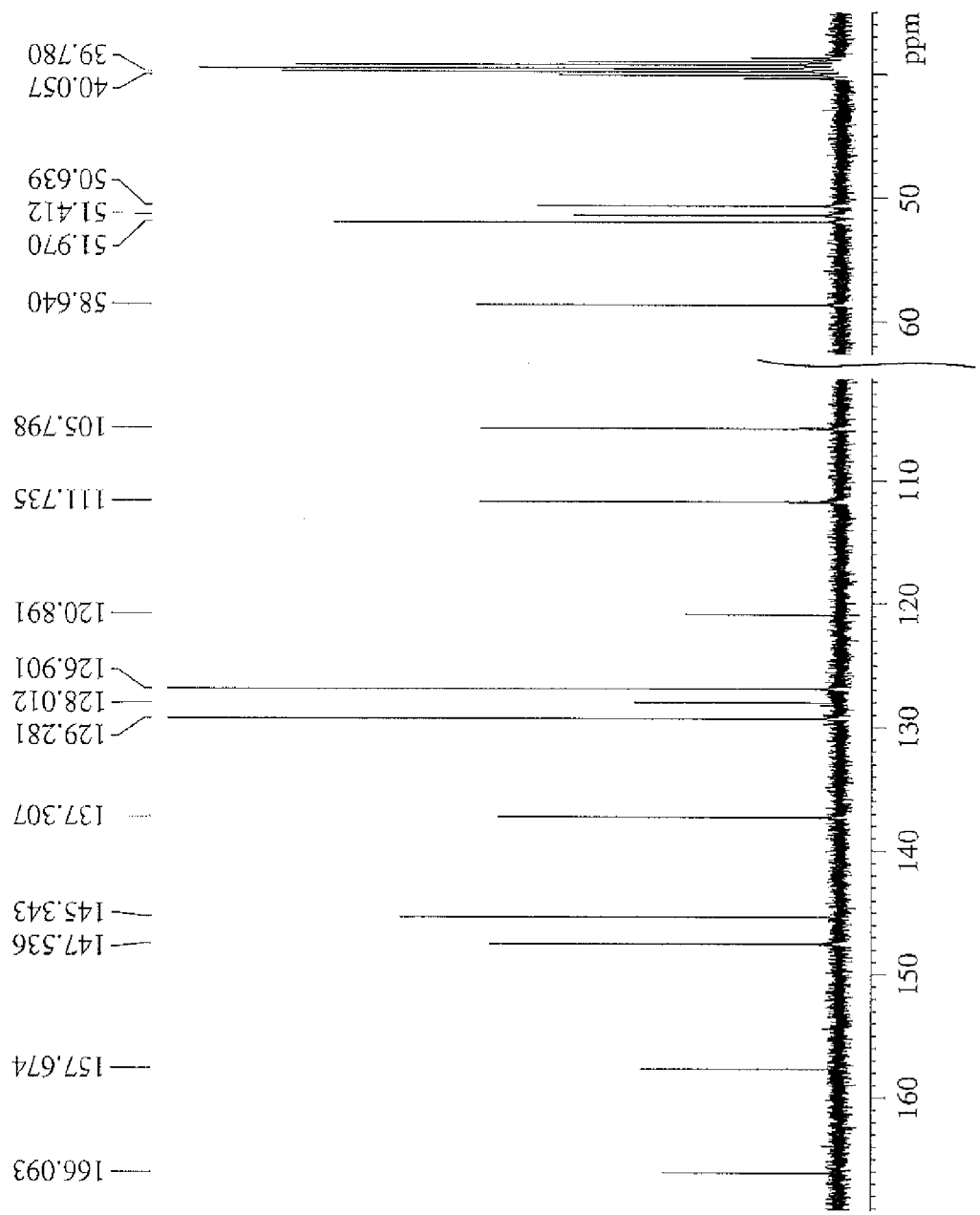

The use of a new compound in accordance with the invention procedure for blocking a hydroxyl function raises the durability of a blocking group a temperature of 20° C., and does not create an additional symmetric centre. Table 1 presents a comparison of compounds which are described in specialist literature [1], and which exhibit similar thermolabile properties, with the examples of the compounds used with the invention. Especially important for the durability of groups is the $R^8$ substituent in position 6 of the pyridyl ring. Placed near the nucleophilic centre, the substituent covers the ring, affecting its stability at a temperature of 15-25° C. Increasing temperature brings about rotation around the bonds, loosens the structure, and in consequence uncovers the pyridyl nucleophilic centre. The use of an electron-donor substituent enhances the nucleophilic properties of the centre, expediting thermal unblocking at higher temperatures. As a result, the procedure improves the blocking durability of the thermolabile protective group at a room temperature, and speeds up the unblocking time while the temperature is raised.

compound was characterized by means of the $^1$HNMR and $^{13}$CNMR spectra presented in FIG. 5. 19.5 g were obtained (a yield of 85%.

EXAMPLE 2

N-pyridyl-N-benzyl-ethanolamine (1 millimole-228 mg) obtained in the manner described in example 1 was dissolved in 5 ml of dry acetonitrile and mixed with 1,1'-carbonyldiimidazole (1.3 mole-210.6 mg). A new compound of formula 16 was obtained as a result of the reaction.

EXAMPLE 3

A. Blocking a Hydroxyl Group

The compound obtained in situ in the manner described in example 2 was made to react with a free primary hydroxyl group of 3'-acetyl-thymidine (0.8 mole-232 g) in the presence of 0.05 ml of 1,1,3,3-tetramethylguanidine. As a result of this reaction, the compound of formula 24 was obtained, with the primary hydroxyl group blocked. Using a new compound to block a hydroxyl function raises the durability of a blocking group at a temperature of 20° C. and does not create an additional asymmetric centre. This comparison is shown in table 1.

B. Unblocking a Hydroxyl Group

In order to remove the group blocking the hydroxyl function, the compound of formula 24 was heated up to a temperature of 90° C. in a dissolving environment, namely a mixture of acetonitrile and a water buffer of a pH of 7 in the

TABLE 1

| No. | Name | % unblocked after 24 hours at. 20° C. | Presence of a chiral centre | Time needed for complete unblocking | % that underwent reaction after 10 minutes | Source of data |
| --- | --- | --- | --- | --- | --- | --- |
| 1. | 2-[N-pyridyl-N-methyl]-1-1phenylcarboxyethylamine | 10% | YES | 15 minutes | 75% | [1] |
| 2. | 2-[N-pyridyl-N-methyl]-1-carboxyethylamine | 8% | YES | 30 minutes | 45% | |
| 3. | 2-[N-pyridyl-N-benzyl]-1-carboxyethylamine | 3% | NO | 4 minutes | 100% | Solution based on the invention |
| 4. | 2-[N-pyridyl-N-(2,4-difluorine)benzyl]-1-carboxyethylamine | 2% | NO | 6 minutes | 100% | |

The examples below elucidate the invention without limiting its scope.

EXAMPLE 1

N-pyridyl-N-benzylamino-ethanol of formula 8

2-bromopyridyne (0.1 mole-15 g) was dissolved in 15 ml of xylene and placed in a flask together with N-benzyl-ethanolamine (0.13 mole-20.9 g), and then the compounds were heated under a reflux condenser for 24 hours at a temperature of 160° C. The product of this reaction was purified in a column filled with silica gel 60 of a particle size 70-230 mesh. Methanol gradient in methylene chloride was used as an eluting phase. Then the fractions containing the product of reaction (N-benzyl-N-pyridyl-ethanolamine) were isolated and combined. The excess of solvent was evaporated. The following volume proportions: 25% of acetonitrile and 75% of the water buffer of a pH of 7. The unblocking yielded the initial 3'-acetyl-thimidine, with the primary hydroxyl group freed.

Figure 3:
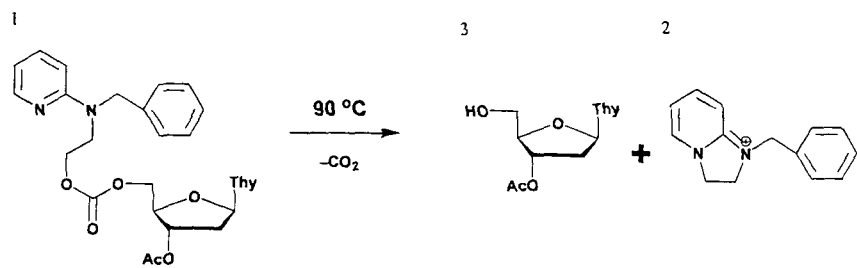
FIG. 3 is an illustration of the products (and by-products) of an intermolecular thermal cyclisation reaction of the depicted compound.

FIG. 1 shows the kinetic decomposition of the compound—as presented in the diagram of FIG. 3—into individual products, as based on a HPLC analysis, where 1 stands for 3'-acetyl-thimidine with the primary hydroxyl function blocked; 2 stands for a cyclic compound, which is a by-product of the intermolecular thermal cyclisation presented in FIG. 3; and 3 denotes the acetylated thimidine with a free hydroxyl function. The analysis was carried out in the following conditions: 3 micron Oligo-RP Clarity column with a linear gradient of 1% acetonitrile/min; buffer A 0.1 M—triethyl acetate, pH=7; velocity of flow—0.75 ml/m When set beside other known solutions, the one based on the invention made it possible to considerably shorten the time necessary for removing a new compound from a hydroxyl function. The comparison is presented in table 1.

EXAMPLE 4

N-pyridyl-N-[2,4-difluorinebenzyl]aminoethanol of formula 9

Figure 6A:
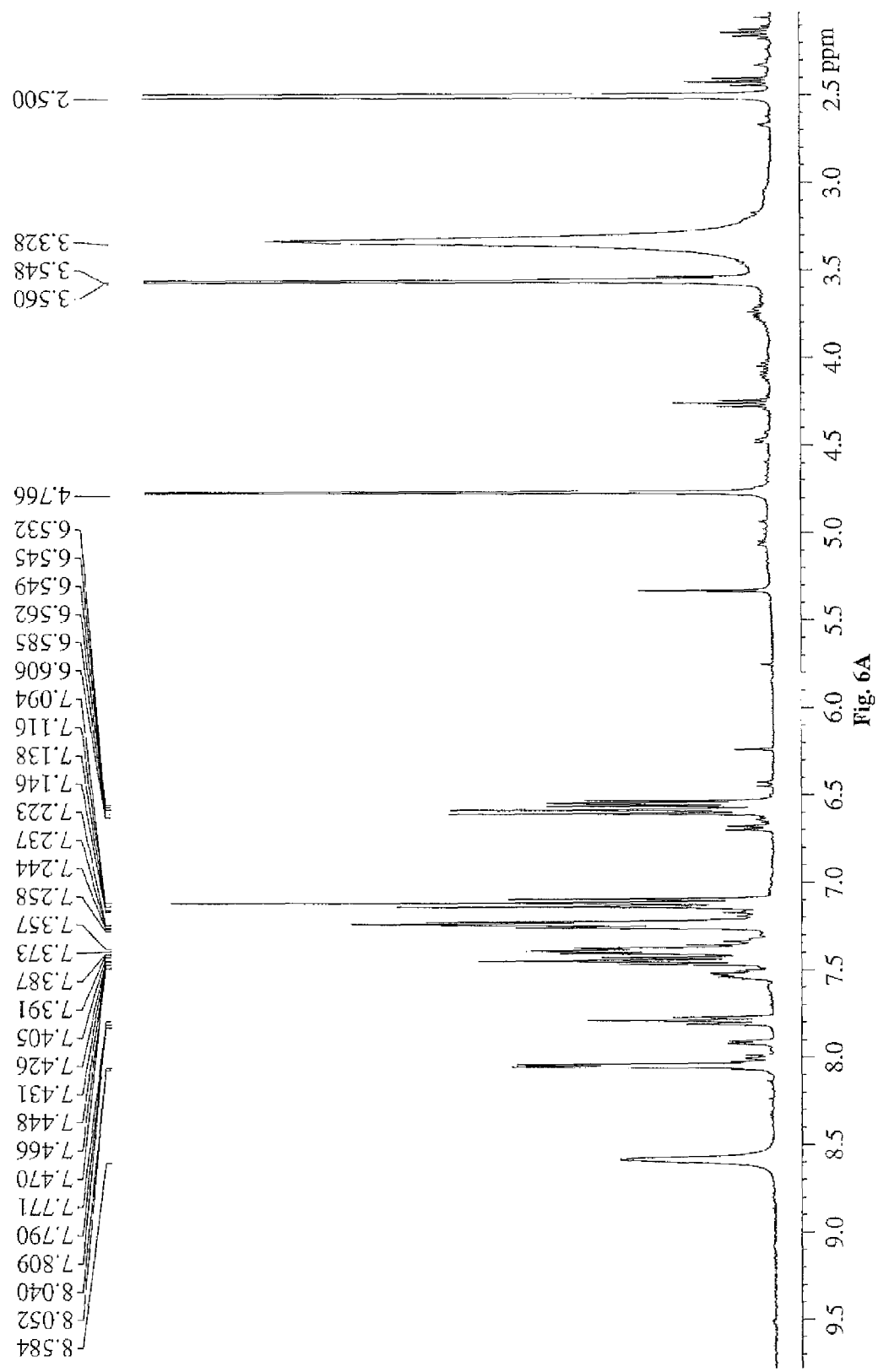
FIGS. 6A and 6B are illustrations of the $^1$HNMR and $^{13}$CNMR spectra of the compound obtained from Example 4.
Figure 6B:
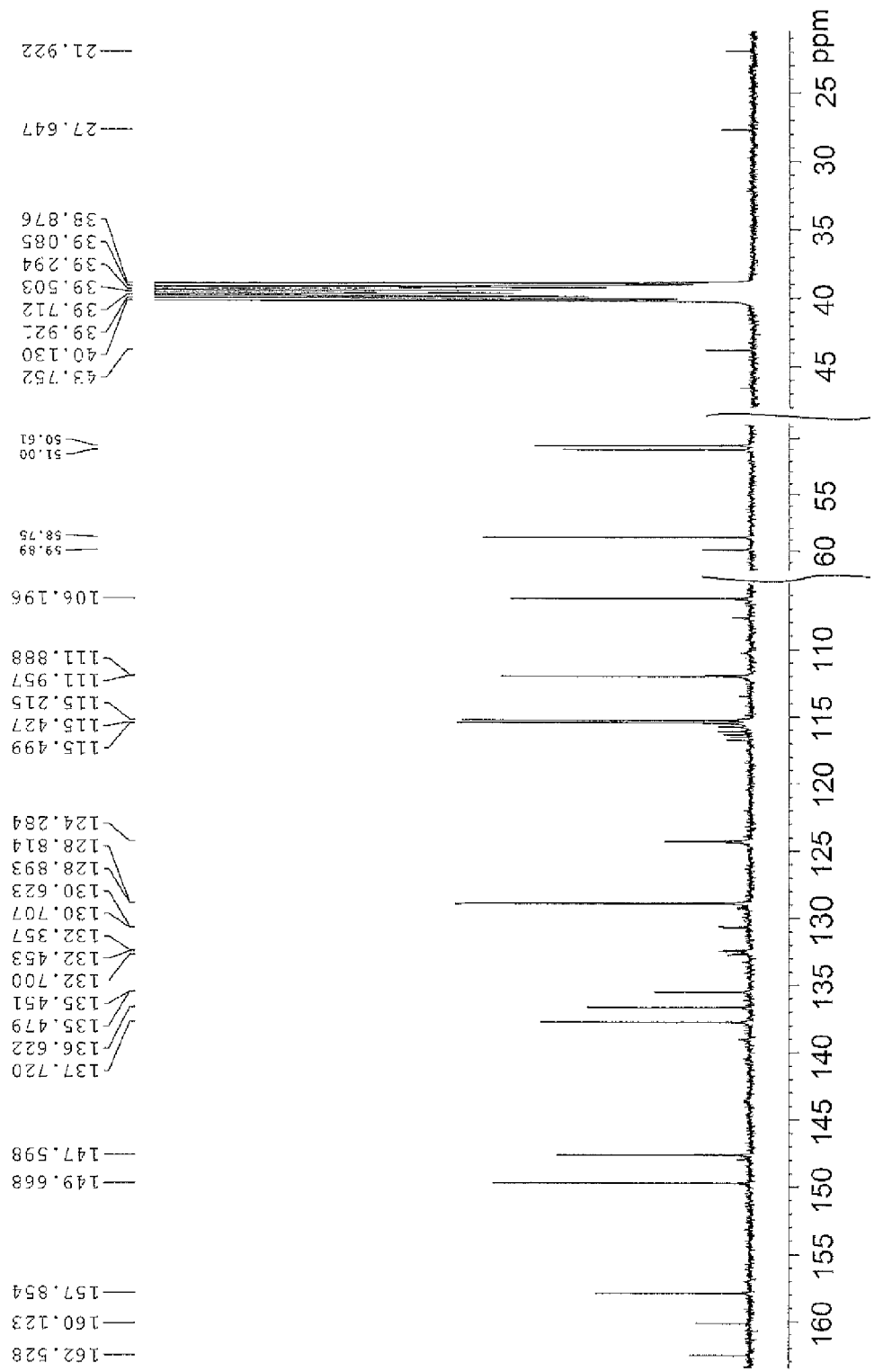

Difluorinephenyl bromide (0.1 mol-19.3 g) was dissolved in 20 ml of tetrahydrofuran and placed in a flask together with N-pyridylethanolamine (0.05 mole-6.9 g) and 0.4 ml of catalytic triethylamine, and then left for 96 hours at a room temperature. The product of this reaction was purified in a column filled with silica gel 60 of a particle size 70-230 mesh. Methanol gradient in methylene chloride was used as an eluting chase. Then the fractions containing the product of the reaction (N-pyridyl-N-difluourine-benzyl-ethanolamine) were isolated and combined. The excess of solvent was evaporated. The compound was characterized by means of the $^1$HNMR, and $^{13}$CNMR spectra and presented in FIG. 6. 184.5 g were obtained (a yield of 72%).

EXAMPLE 5

N-pyridyl-N-[2,4-difluorinebenzyl]aminoethanol, obtained as is described in example 4, was made to react in the manner shown in example 2. A compound of formula 17 was obtained as a result of this reaction.

EXAMPLE 6

A. Blocking a Hydroxyl Group

A compound obtained in situ as described in the example 4 was made to react in the manner presented in the example 5. A compound of formula 25 was obtained as a result of this reaction, with the primary hydroxyl group blocked.

B. Unblocking a Hydroxyl Group

The method described in the example 3 was used to unblock the hydroxyl group. After unblocking, the initial compound was obtained, with the hydroxyl group freed.

Figure 2:
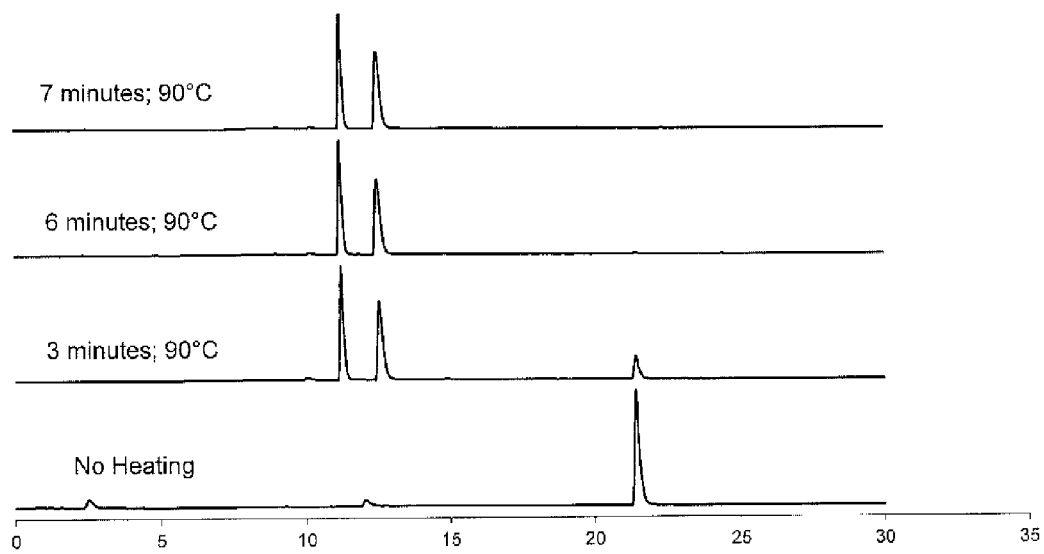
FIG. 2 is an illustration of the kinetic decomposition (based on a HPLC analysis) of the compound depicted in FIG. 4.
Figure 4:
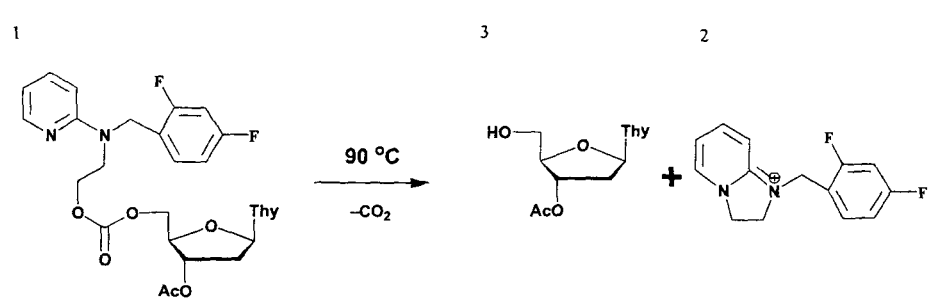
FIG. 4 is an illustration of the products (and by-products) of an intermolecular thermal cyclisation reaction of the depicted compound.

FIG. 2 shows the kinetic decomposition of the compound—as presented in the diagram in FIG. 4—into individual products, as based on a HPLC analysis, where 1 stands for 3'-acetyl-thimidine with the primary hydroxyl function blocked; 2 stands for a cyclic compound, which is a by-product of intermolecular thermal cyclization presented in FIG. 4; and 3 denotes the acetylated thymidine with a free hydroxyl function. The analysis was carried out in the following conditions: 3 micron Oligo-RP Clarity column with a linear gradient of 1% acetonitrile/min; buffer A 0.1 M—triethyl acetate, pH=7; velocity of flow—0.75 ml/m.

When compared with other solutions, this one made it possible to considerably shorten the time needed for removing a new compound from a hydroxyl function. The comparison is presented in table 1.

EXAMPLE 7

Figure 7A:
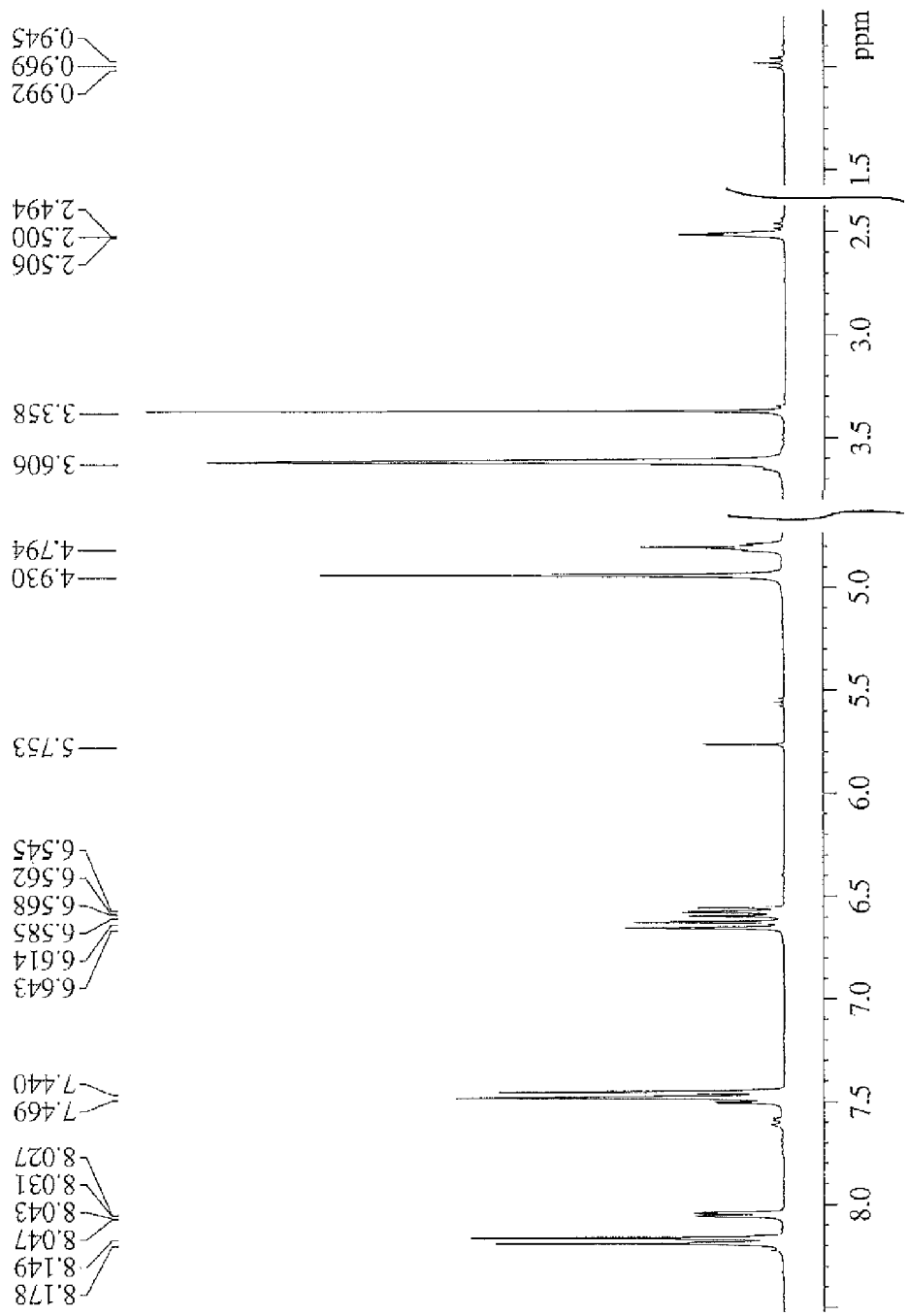
FIGS. 7A and 7B are illustrations of the $^1$HNMR and $^{13}$CNMR spectra of the compound obtained from Example 7.
Figure 7B:
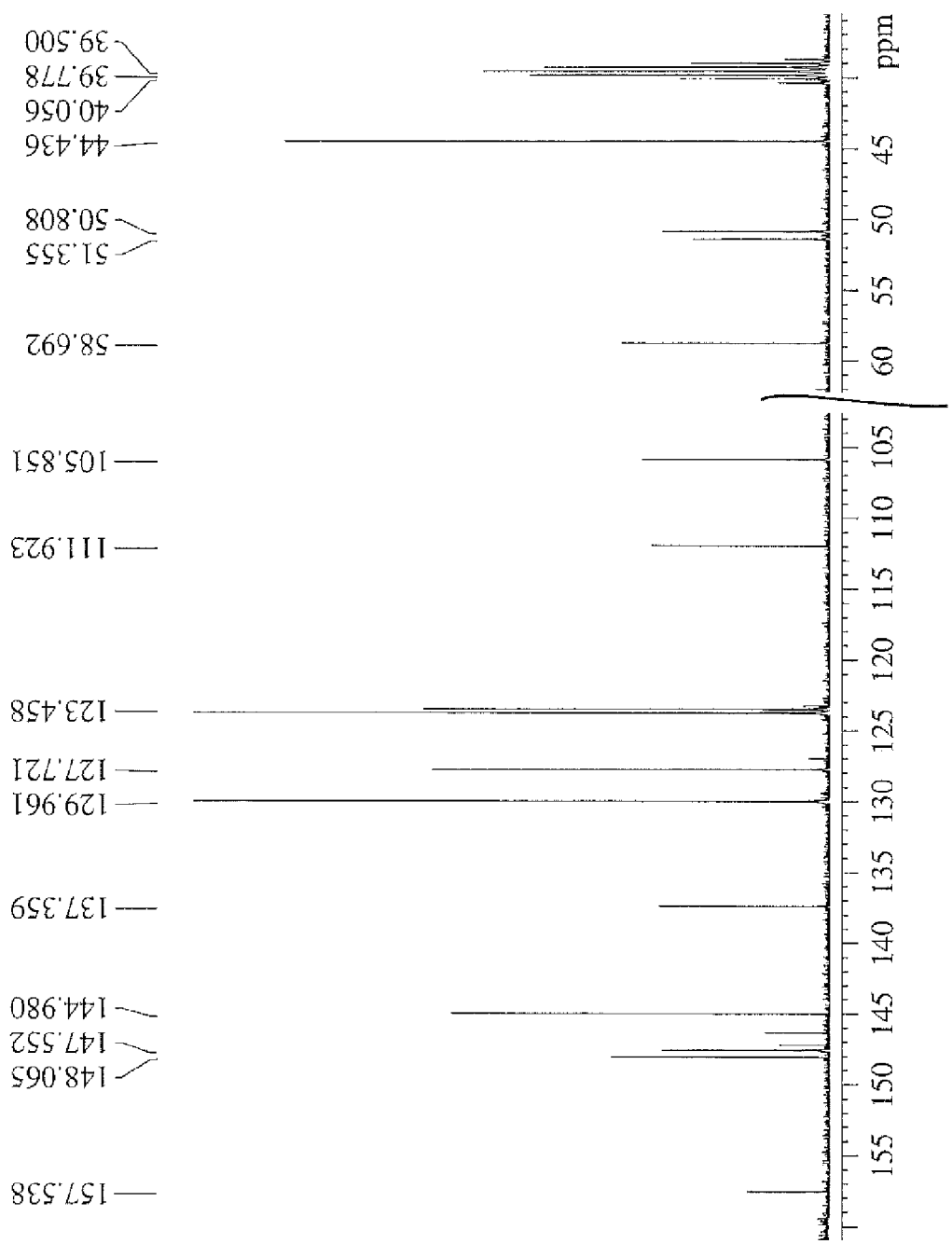

N-pyridyl-N-[4-nitrobenzyl]aminoethanol of formula 10 is obtained as is described in the example 4. The compound was characterized by means of the $^1$HNMR, and $^{13}$CNMR spectra, presented in FIG. 7.

EXAMPLE 8

N-pyridyl-N-[4-nitrobenzyl]aminoethanol obtained as is described in the example 7 was made to undergo reaction shown in the example 2. A new compound of general formula 18 was obtained as a result of this reaction.

EXAMPLE 9

A. Blocking a Hydroxyl Group

A compound obtained in situ as is described in the example 8 was made to undergo reaction shown in the example 3. A compound of formula 26 was obtained as a result of this reaction, with the primary hydroxyl group blocked.

B. Unblocking a Hydroxyl Group

The method described in the example 3 was used to unblock the hydroxyl group. After unblocking, the initial compound was obtained, with the hydroxyl group freed.

EXAMPLE 10

N-(6-methyl-pyridyl)-N-benzyl-aminoethanol of formula 11

Figure 8A:
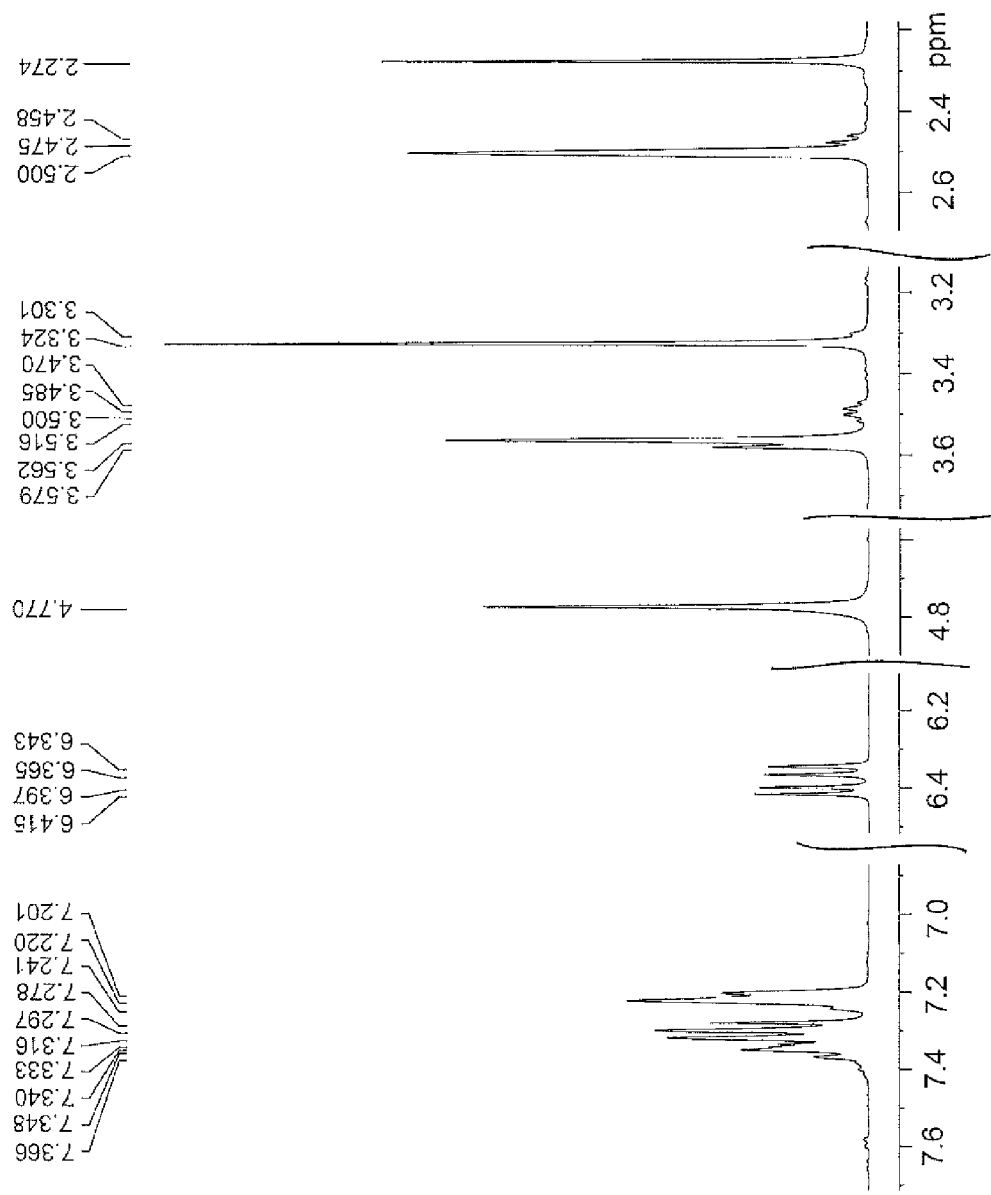
FIGS. 8A and 8B are illustrations of the $^1$HNMR and $^{13}$CNMR spectra of the compound obtained from Example 10.
Figure 8B:
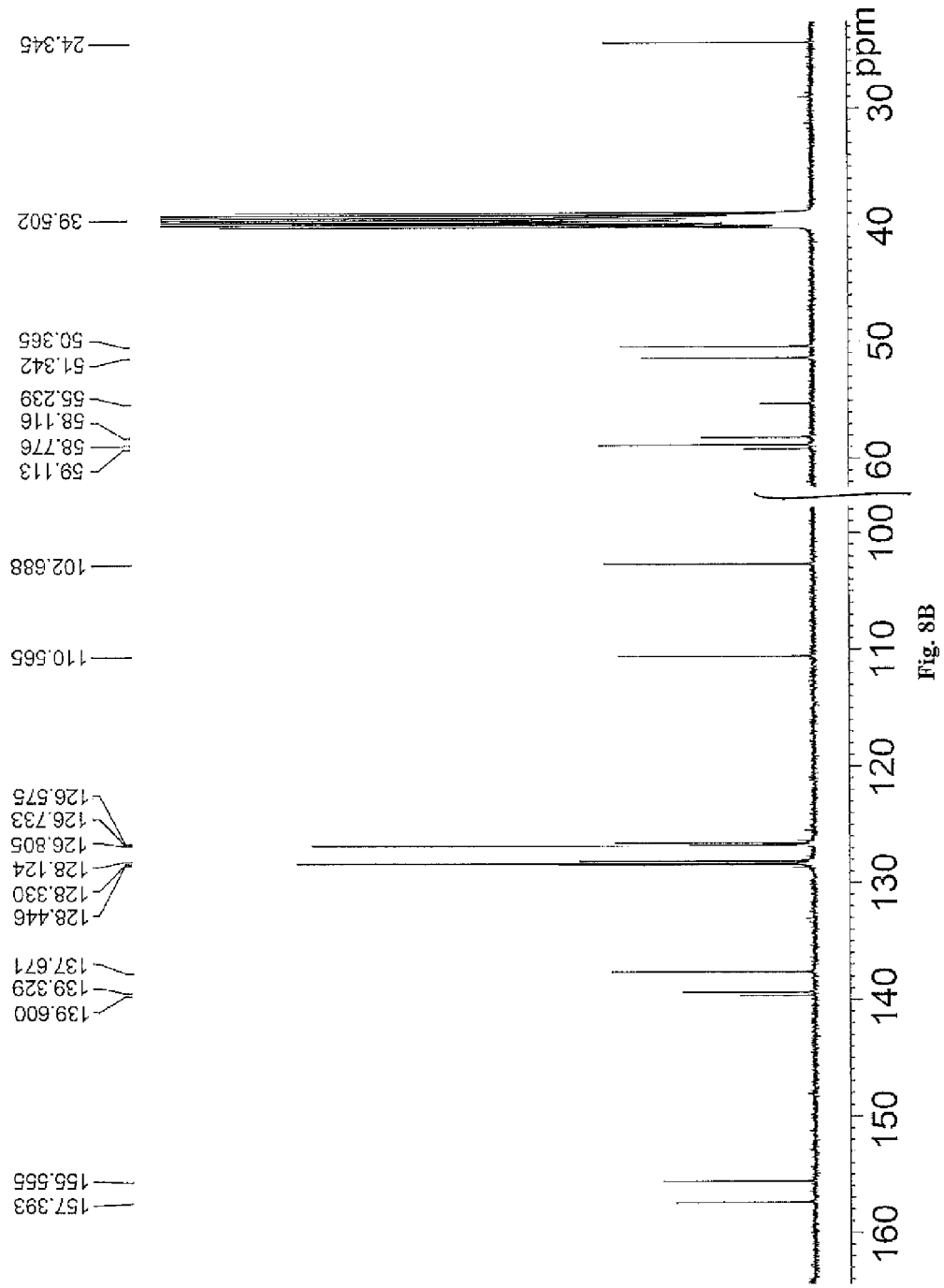

2-bromine-6-methylpyridine (0.1 mol-17.24 g) was dissolved in 18 ml of xylene and placed in a flask together with N-benzylethanolamine (0.3 mole-45.39 g) and 0.5 ml of catalytic diisopropylethylamine. Then the compounds were heated for 48 hours under a reflux condenser at a temperature of 140° C. The product of this reaction was purified in a column filled with silica gel 80 of a particle size 230-400 mesh. Methanol gradient in methylene chloride was used as an eluting phase. Then the fractions containing the product of the reaction (N-(6-methyl-pyridyl)-N-benzylethanolamine) were isolated and combined. The excess of solvent was evaporated. The compound was characterized by means of the $^1$HNMR, the $^{13}$CNMR spectra, presented in FIG. 8. 14.58 g were obtained (a yield of 60%

EXAMPLE 11

N-(6-methyl-pyridyl)-N-benzyl-aminoethanol obtained as is described in the example 10 was made to undergo the reaction presented in the example 2. A new compound of formula 19 was obtained as a result of the reaction.

EXAMPLE 12

A. Blocking a Hydroxyl Group

A compound obtained in situ as is described in the example 11 was made to undergo the reaction presented in the example 3. A compound of formula 27 was obtained as a result of this reaction, with the primary hydroxyl group blocked.

B. Unblocking a Hydroxyl Group

The method described in the example 3 was used to unblock the hydroxyl group. After unblocking, the initial compound was obtained, with the free hydroxyl group.

EXAMPLE 13

N-pyridyl-N-[diphenylmethyl]aminoethanol of formula 12

Figure 9A:
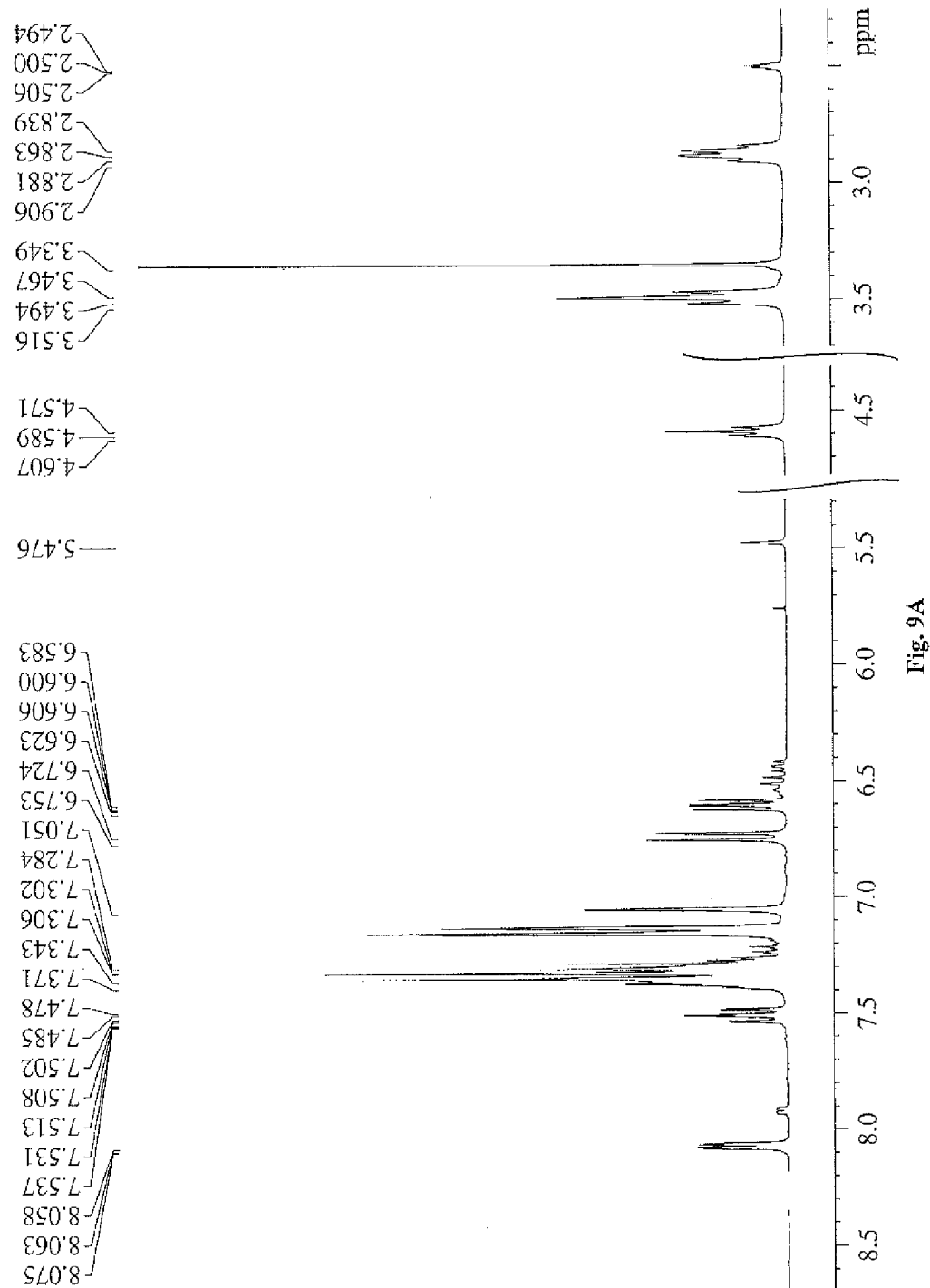
FIGS. 9A and 9B are illustrations of the $^1$HNMR and $^{13}$CNMR spectra of the compound obtained from Example 13.
Figure 9B:
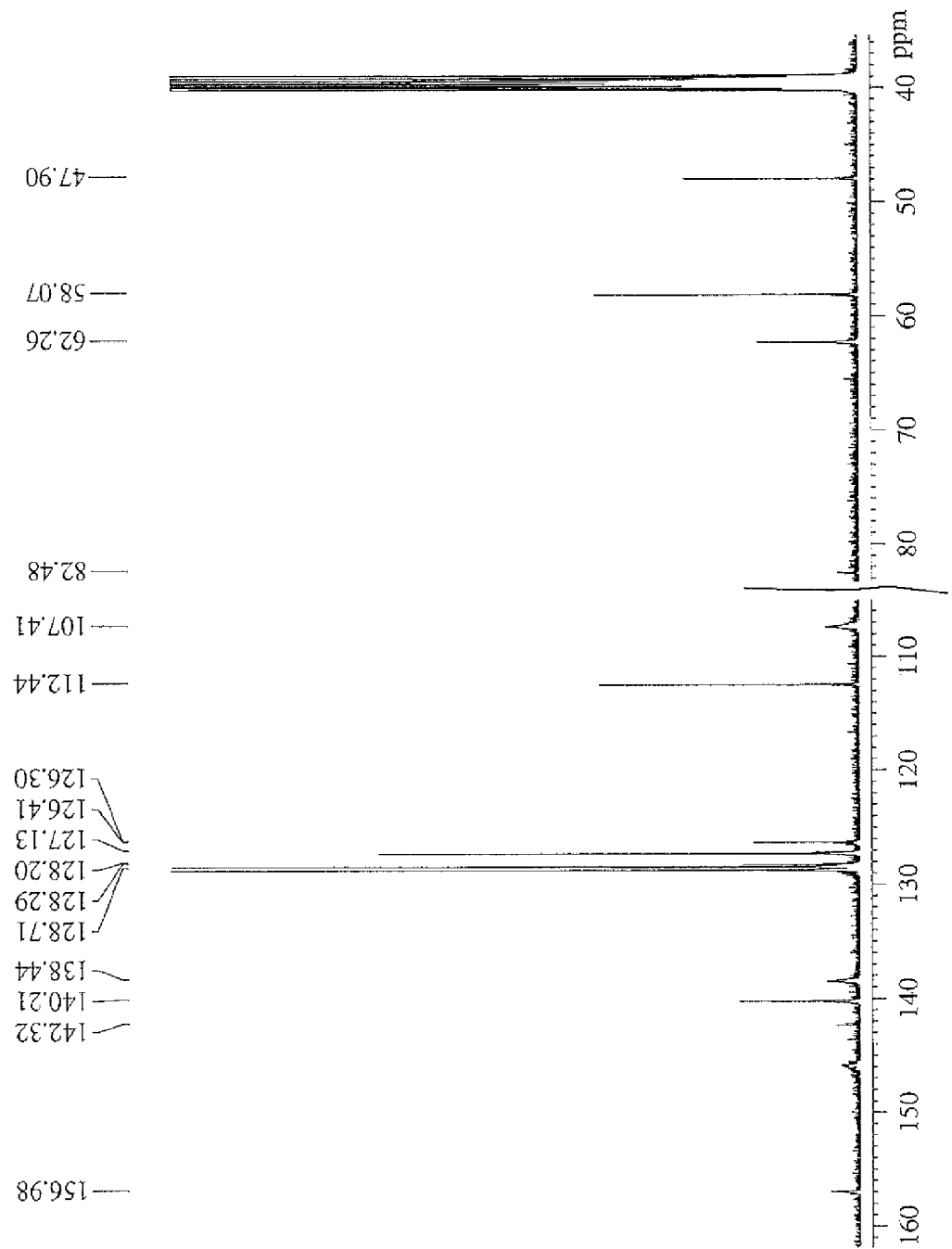

Diphenylmethyl bromide (0.1 mol; 24.75 g) was dissolved in 25 ml of tetrahydrofuran and placed in a flask together with N-pyridylethanolamine (0.05 mole-6.9 g) and 0.5 ml of catalytic N-methylimidazol, and then left for 72 hours in a dryer at temperature of 65° C. The product of this reaction was purified on a column filled with silica gel 60 of a particle size 70-230 mesh. Methanol gradient in methylene chloride was used as an eluting phase. Then the fractions containing the product of the reaction (N-pyridyl-N-[diphenylmethyl]aminoethanol) were isolated and combined. The excess of solvent was evaporated. The compound was characterized by means of the $^1$HNMR and $^{13}$CNMR spectra, presented in FIG. 9. 19.03 g were obtained (a yield of 62%).

EXAMPLE 14

N-pyridyl-N-[diphenylmethyl]aminoethanol (1 millimole; 304 mg) obtained as described in the example 13 was dissolved in 5 ml of dry acetonitrile and mixed with 1,1'-carbonyldiimidazole (1.3 millimole; 210.6 mg). A new compound of formula 20 was obtained as a result of the reaction.

EXAMPLE 15

A. Blocking a Hydroxyl Group

The compound obtained in situ as described in the example 14 was made to undergo reaction with the free primary hydroxyl group of 3'-acetyl-thymidine (0.8 mole-232 g) in the presence of 0.05 ml 1,1,3,3-tetramethylguanidine. As a result of this reaction, the compound of formula 28 was obtained, with the primary hydroxyl group blocked. Using a new compound to block a hydroxyl function raises the durability of a blocking group at a temperature of 20° C. and does not create an additional asymmetric centre.

B. Unblocking Hydroxyl Group

In order to remove the group blocking the hydroxyl function, the compound was heated up to a temperature of 90° C. in a dissolving environment, namely a mixture of acetonitrile and a water buffer of a pH of 7 in the following volume proportions: 25% of acetonitrile and 75% of the water buffer of a pH of 7. The unblocking yielded the initial 3'-acetyl-thimidine, with the primary hydroxyl group freed and the remnant of the blocking group.

EXAMPLE 16

Figure 10B:
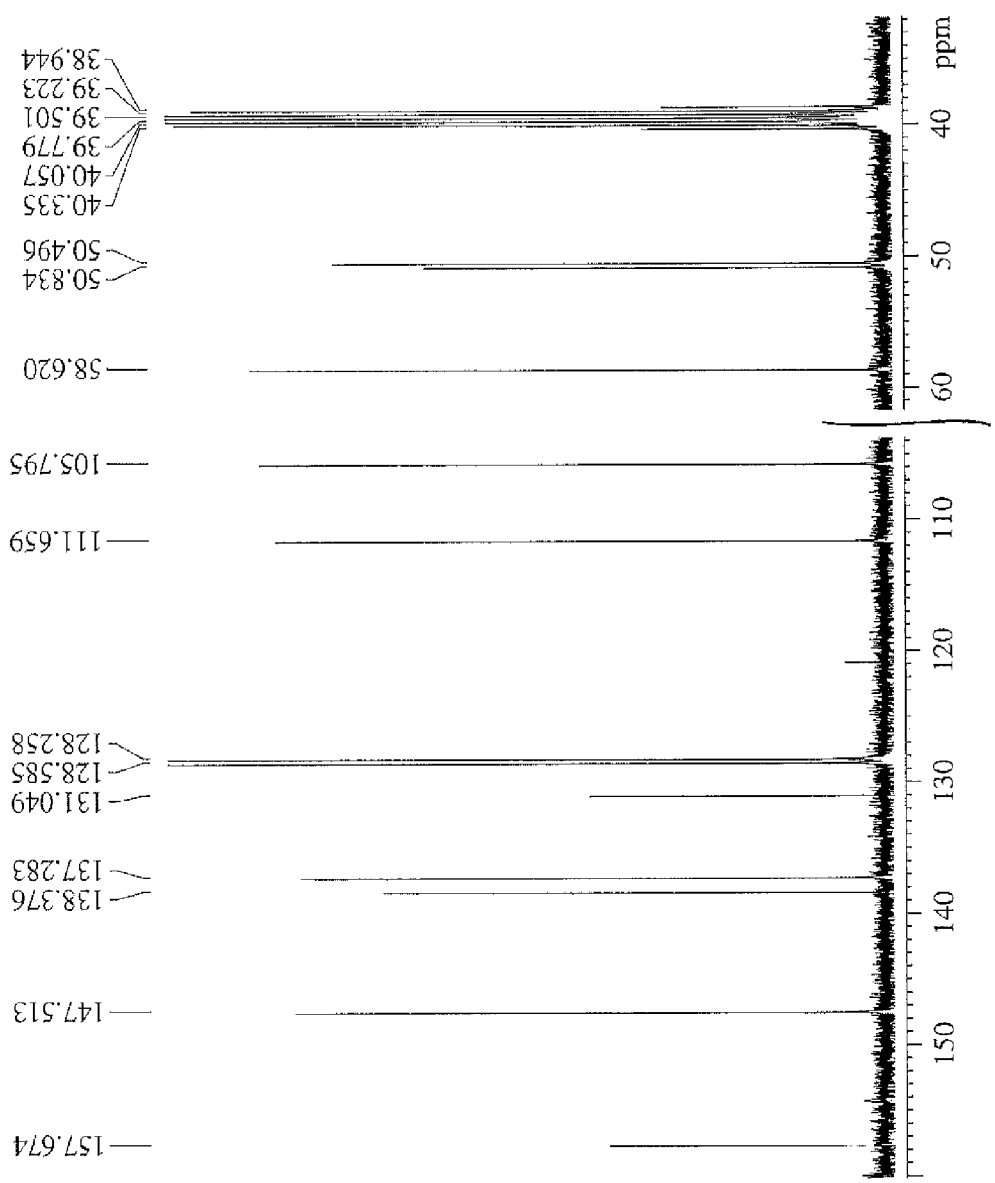

N-pyridyl-N-[4-chlorobenzyl]aminoethanol of formula 13 was obtained in the manner described in the example 4. The compound was characterized by means of the $^1$HNMR and $^{13}$CNMR spectra, presented in FIG. 10.

EXAMPLE 17

N-pyridyl-N-[4-chlorobenzyl]aminoethanol obtained in the manner described in the example 16 was made to undergo the reaction presented in the example 2. A new compound of formula 21 was obtained as a result of the reaction.

EXAMPLE 18

A. Blocking a Hydroxyl Group

The compound obtained in situ as is described in the example 17 was made to undergo the reaction presented in the example 3. As a result of the reaction, a compound of formula 29 was obtained, with the primary hydroxyl group blocked.

B. Unblocking a Hydroxyl Group

The method described in the example 3 was used to unblock the hydroxyl group. After unblocking, the initial compound was obtained, with the hydroxyl group freed.

EXAMPLE 19

Figure 11A:
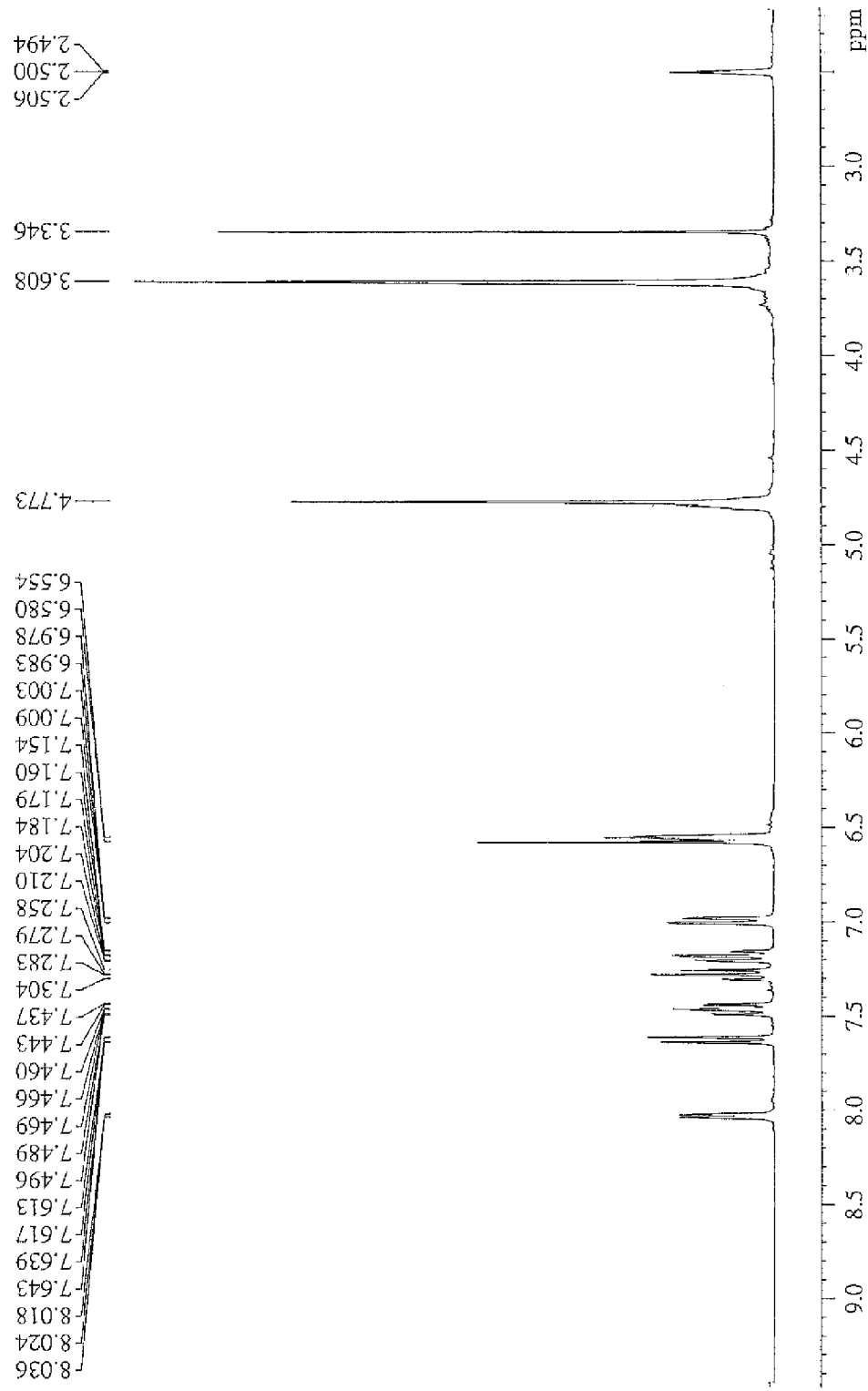
FIGS. 11A and 11B are illustrations of the $^1$HNMR and $^{13}$CNMR spectra of the compound obtained from Example 19.
Figure 11B:
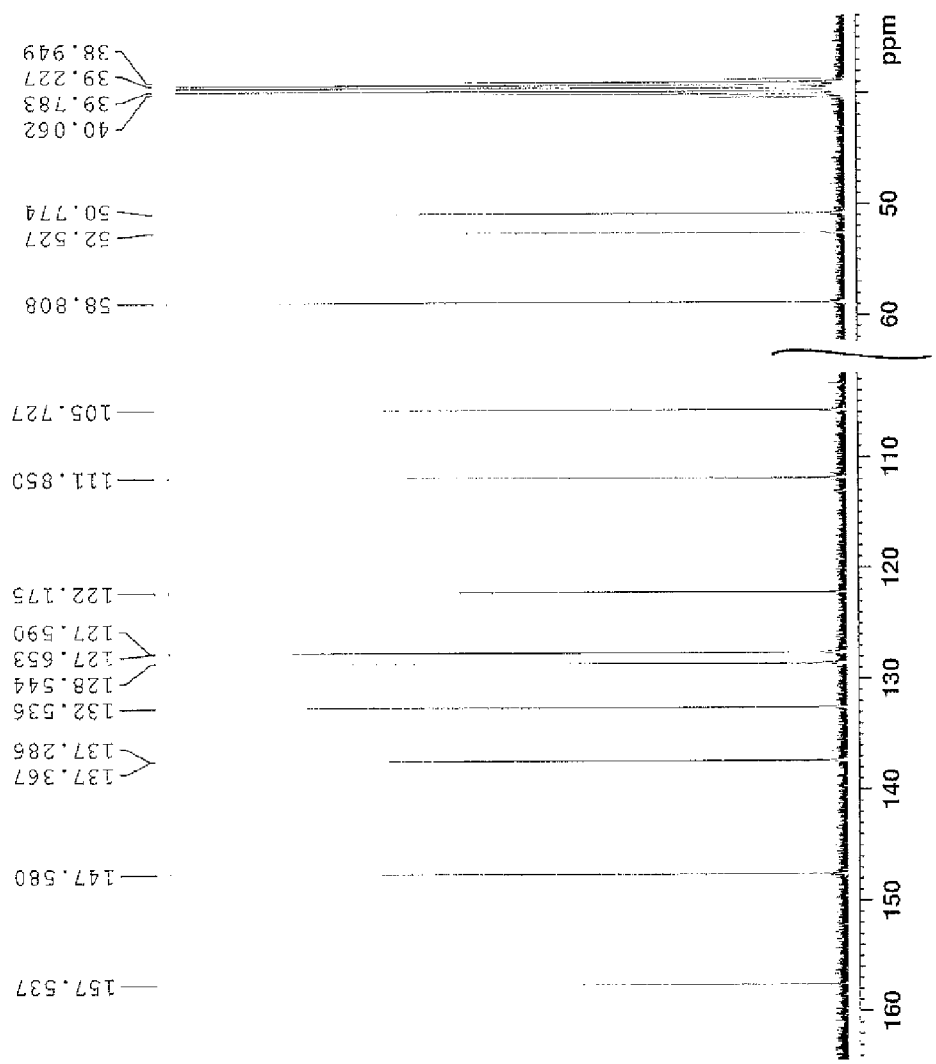

N-pyridyl-N-[4-bromobenzyl]aminoethanol of formula 14 was obtained in the manner described in the example 4. The compound was characterized by means of the $^1$HNMR and $^{13}$CNMR spectra, presented in FIG. 11.

EXAMPLE 20

N-pyridyl-N-[2-bromobenzyl]aminoethanol obtained in the manner described in the example 19 was made to undergo the reaction presented in the example 2. A new compound of formula 22 was obtained as a result of the reaction.

EXAMPLE 21

A. Blocking a Hydroxyl Group

The compound obtained in situ in the manner described in the example 20 was made to undergo the reaction presented in the example 3. As a result of the reaction, a compound of formula 30 was obtained, with the primary hydroxyl group blocked.

B. Unblocking a Hydroxyl Group

The method described in the example 3 was used to unblock the hydroxyl group. After unblocking, the initial compound was obtained, with the free hydroxyl group.

EXAMPLE 22

Figure 12A:
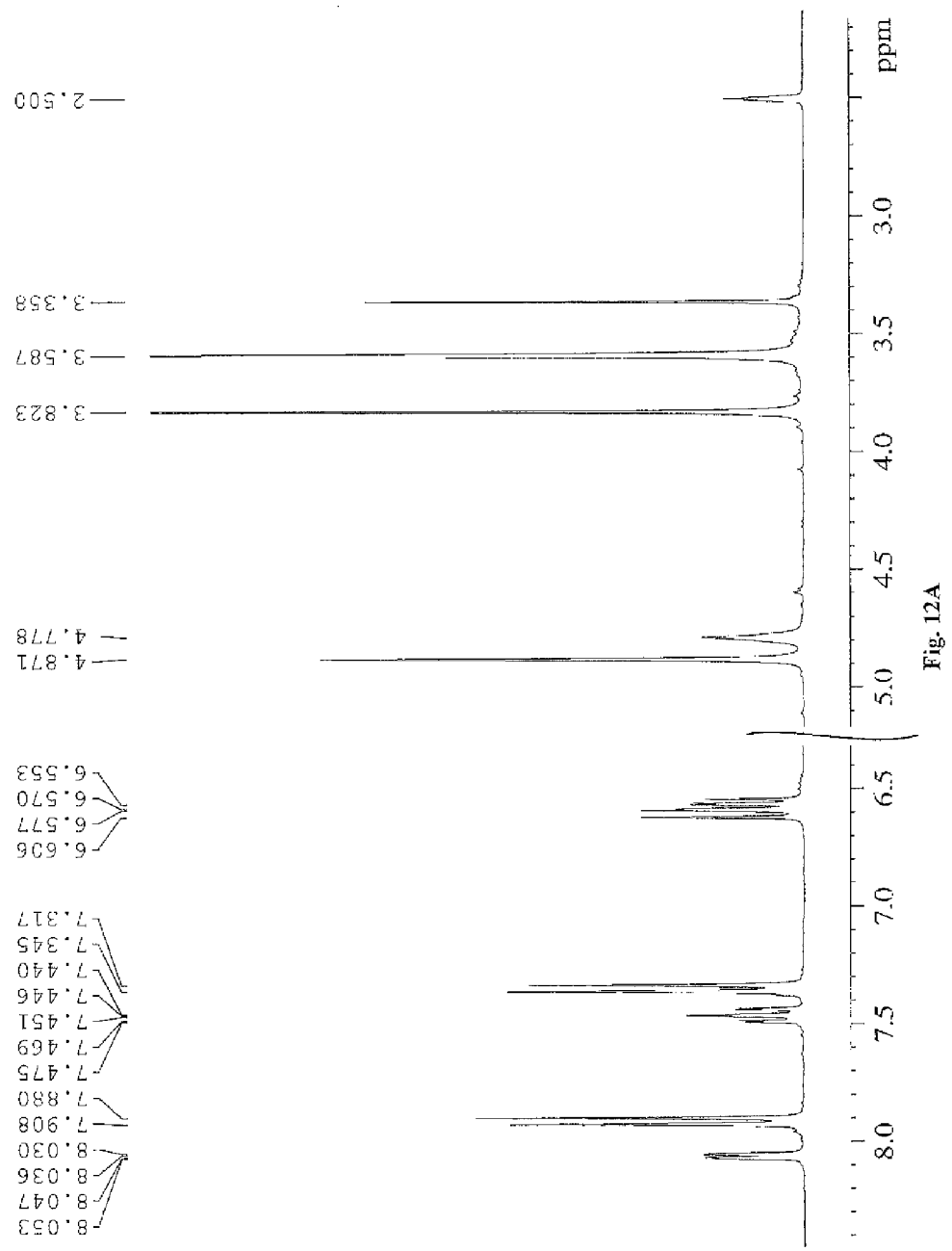
FIGS. 12A and 12B are illustrations of the $^1$HNMR and $^{13}$CNMR spectra of the compound obtained from Example 22.
Figure 12B:
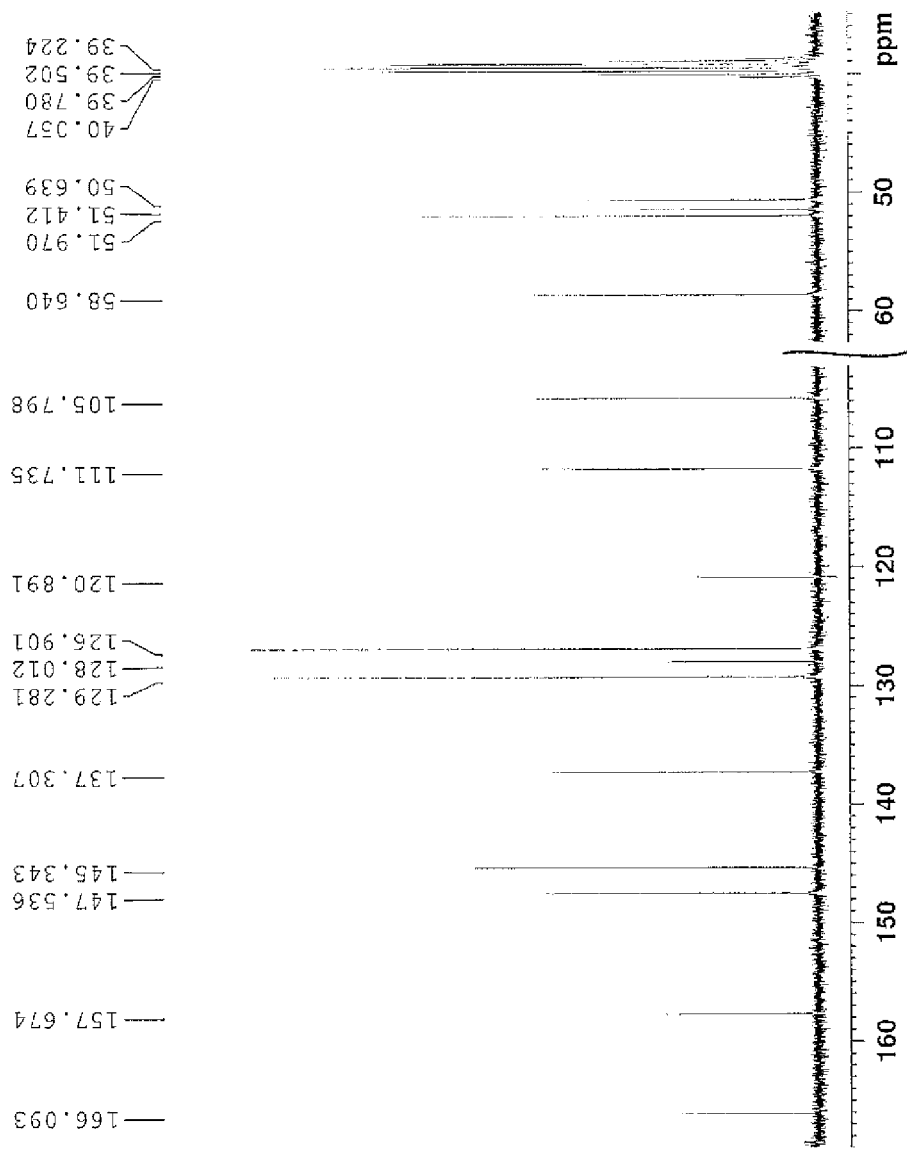

N-pyridyl-N-[4-(methoxycarboxyl)benzyl]aminoethanol of formula 15 was obtained in the manner described in the example 4. The compound was characterized by means of the $^1$HNMR and $^{13}$CNMR spectra, presented in FIG. 12.

EXAMPLE 23

N-pyridyl-N-[4-(methoxycarboxyl)benzyl]aminoethanol obtained as described in the example 22 was made to undergo the reaction presented in the example 2. A new compound of formula 23 was obtained as a result of the reaction.

EXAMPLE 24

A. Blocking a Hydroxyl Group

The compound obtained in situ in the manner described in the example 23 was made to undergo the reaction presented in the example 3. As a result of the reaction, a compound of formula 31 was obtained, with the primary hydroxyl group blocked B. Unblocking a Hydroxyl Group The method described in the example 3 was used to unblock the hydroxyl group. After unblocking, the initial compound was obtained, with the free hydroxyl group.

BIBLIOGRAPHY

[1]—Chmielewski M. K., Marchan V., Cieslak J., Grajkowski A., Livengood V., Munch U., Wilk A., Beaucage S. L., J. Org. Chem. 2003, 68, 10003-10012

The invention claimed is:

1. A compound of general formula 1,

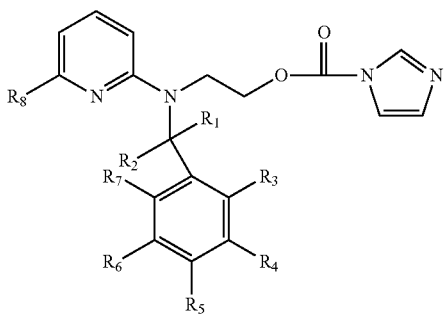

where
- $R^1$ stands for H or $CH_3$, O, NH, $C_6H_5$, $CH_2C_6H_5$;
- $R^2$ stands for H;
- $R^3$, $R^4$, $R^5$, $R^6$, $R^7$ are equal or different and stand for H or $NH_2$, OH, $OCH_3$, $NO_2$, $C(O)OCH_3$, $C(O)OC_2H_5$, a halogen;
- $R^8$ denotes $CH_3$, OH or $CH_2OH$, O, an alkene with the main chain containing 1-5 carbon atom(s), and with one double bond, $CH(CH_3)C_6H_5CH_3CH_2C_6H_5$, $CH_3NR^9$, where $R^9$ stands for H or $CH_3$, O, NH, $C_6H_5$, $CH_2C_6H_5$.

2. A protected molecule of general formula 3,

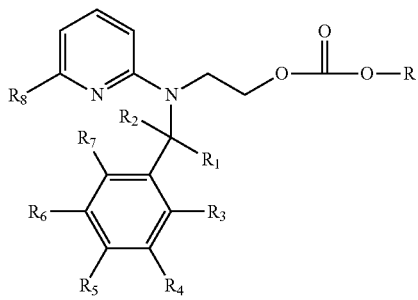

where
- $R^1$ stands for H or $CH_3$, O, NH, $C_6H_5$, $CH_2C_6H_5$;
- $R^2$ stands for H;
- $R^3$, $R^4$, $R^5$, $R^6$, $R^7$ are equal or different and stand for H or $NH_2$, OH, $OCH_3$, $NO_2$, $C(O)OCH_3$, $C(O)OC_2H_5$, a halogen;
- $R^8$ denotes $CH_3$, OH or $CH_2OH$, O, an alkene with the main chain containing 1-5 carbon atom(s), and with one double bond, $CH(CH_3)C_6H_5$, $CH_3NR^9$, where $R^9$ stands for H or $CH_3$, O, NH, $C_6H_5$, $CH_2C_6H_5$; R stands for the rest of the protected molecule.

3. A method of protecting a hydroxyl function of a molecule with a thermolabile group comprising reacting the molecule with a compound of general formula 1,

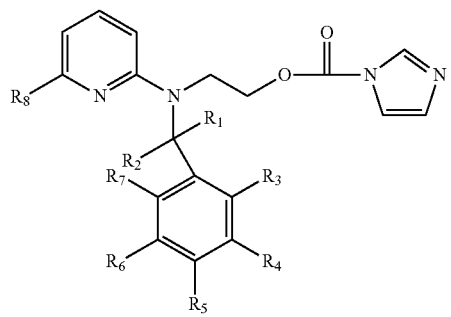

in the presence of a chemically basic catalyst in order to block the hydroxyl function, yielding a protected molecule of general formula 3,

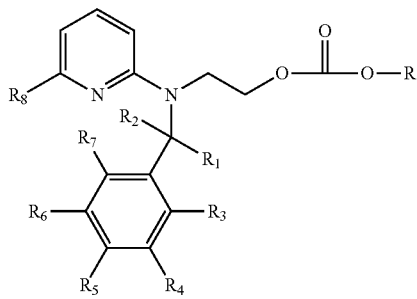

wherein
- $R^1$ is H, $CH_3$, $O^-$, NH, $C_6H_5$, or $CH_2C_6H_5$;
- $R^2$ is H;
- $R^3$, $R^4$, $R^5$, $R^6$ and $R^7$ are the same or different and denote H, $NH_2$, OH, $OCH_3$, $NO_2$, $C(O)OCH_3$, $C(O)OC_2H_5$, or a halogen;
- $R^8$ is $CH_3$, OH, $CH_2OH$, $O^-$, an alkene with the main chain containing 1-5 carbon atom(s) and with one double bond, $CH(CH_3)C_6H_5$, or $CH_3NR^9$, where $R^9$ is H, $CH_3$, $O^-$, NH, $C6H_5$, or $CH_2C_6H_5$; and
- R is the rest of the molecule protected during the reaction, wherein the thermolabile protecting group may be unblocked in a solvent at a temperature of 50-95° C.

4. A method of claim 3 wherein the molecule is a nucleoside, nucleotide oligomer or nucleic acid.

5. The method according to claim 3, wherein a compound of general formula 1 is used, where $R^1$ stands for H; $R^2$ stands for H; $R^3$, $R^4$, $R^5$, $R^6$, $R^7$ are equal and stand for H; $R^8$ stands for $CH_3$.

6. The method according to claim 3, wherein the unblocking is carried out at a temperature of 70-90° C.

7. The method according to claim 3, wherein a solvent can be made up of acetonitrile; or a homogenous mixture of alcohol and water; or a water buffer of a pH of 6-8; or a mixture of acetonitrile and a water buffer of a pH of 6-8, the volume fraction of the former being 5% to 50%, and the concentration of the blocked form in the mixture being 0.5 mole to 0.01 millimole; or a mixture of alcohol with a water buffer of a pH of 6-8, the volume fraction of the former being 5% to 50%, and the concentration of the blocked form in the mixture being 0.5 mole to 0.01 millimole.

8. The method according to claim 7, wherein at the volume fraction of acetonitrile is 10% to 30% in its mixture with a water buffer.

9. The method according to claim 7, wherein the volume fraction of alcohol is 10% to 30% in its mixture with a water buffer.

10. The method according to claim 7, wherein the water buffer has a pH of 7.

11. The method according to claim 7, wherein the mixture of acetonitrile with a water buffer has a pH of 7.

12. The method according to claim 7, wherein the mixture of an alcohol with a water buffer has a pH of 7.

13. The method according to claim 7, wherein concentration of the blocked form is 0.2 mole to 1 millimole in the mixture of acetonitrile with a water buffer.

14. The method according to claim 7, wherein the concentration of the blocked form is 0.2 mole to 1 millimole in the mixture of an alcohol with a water buffer.

\* \* \* \* \*